United States Patent
Lechner et al.

(10) Patent No.: US 8,663,204 B2
(45) Date of Patent: Mar. 4, 2014

(54) MEDICAL INSTRUMENT COMPRISING A SEPARATE TRANSMITTER UNIT WHICH CAN BE EXTERIORLY FASTENED

(75) Inventors: Christian Lechner, Jesenwang (DE); Norman Plaβky, Erfurt (DE); Manuel Millahn, München (DE); Georg Christian, München (DE)

(73) Assignee: Brainlab AG, Feldkirchen (DE)

( * ) Notice: Subject to any disclaimer, the term of this patent is extended or adjusted under 35 U.S.C. 154(b) by 342 days.

(21) Appl. No.: 12/768,767

(22) Filed: Apr. 28, 2010

(65) Prior Publication Data

US 2010/0272442 A1   Oct. 28, 2010

Related U.S. Application Data

(60) Provisional application No. 61/173,648, filed on Apr. 29, 2009.

(30) Foreign Application Priority Data

Apr. 28, 2009  (EP) .................................... 09158956

(51) Int. Cl.
*A61B 17/00* (2006.01)
(52) U.S. Cl.
USPC ............................................................. 606/1
(58) Field of Classification Search
USPC .................................................. 607/32, 60
See application file for complete search history.

(56) References Cited

U.S. PATENT DOCUMENTS

| 6,190,395 | B1 * | 2/2001 | Williams ...................... 606/130 |
| 6,468,202 | B1 * | 10/2002 | Irion et al. .................... 600/117 |
| 8,010,181 | B2 * | 8/2011 | Smith et al. ................... 600/424 |
| 2001/0034530 | A1 * | 10/2001 | Malackowski et al. ........ 606/130 |
| 2004/0054489 | A1 * | 3/2004 | Moctezuma De La Barrera et al. ............................ 702/105 |
| 2005/0020909 | A1 * | 1/2005 | Moctezuma de la Barrera et al. ............................ 600/424 |
| 2005/0131426 | A1 * | 6/2005 | Moctezuma de la Barrera et al. ............................ 606/130 |
| 2006/0142740 | A1 * | 6/2006 | Sherman et al. ................... 606/1 |
| 2007/0078328 | A1 * | 4/2007 | Ozaki et al. ................... 600/407 |
| 2007/0239289 | A1 * | 10/2007 | Cambre et al. ................... 700/64 |
| 2008/0281989 | A1 * | 11/2008 | Hager et al. ...................... 710/1 |
| 2010/0121149 | A1 * | 5/2010 | Sholev ........................... 600/118 |

FOREIGN PATENT DOCUMENTS

EP  1 782 744   5/2007
EP  1 990 021   11/2008

* cited by examiner

*Primary Examiner* — Bill Thomson
*Assistant Examiner* — John R Downey
(74) *Attorney, Agent, or Firm* — Tucker Ellis LLP

(57) ABSTRACT

The invention relates to a medical instrument, comprising a signal transmitter and at least one activating device for activating the transmitter which is provided on a transmitter unit which is separate from the instrument, wherein the transmitter unit is a unit which can be fastened to the exterior of the instrument. It also relates to a method for controlling a treatment-assisting medical software by means of a signal transmitter which is arranged on a medical instrument, wherein the instrument is positionally detected by means of a medical tracking system, and wherein the software assigns a different significance to the signal output by the transmitter depending on the position of the instrument.

14 Claims, 3 Drawing Sheets

MEDICAL INSTRUMENT COMPRISING A SEPARATE TRANSMITTER UNIT WHICH CAN BE EXTERIORLY FASTENED

RELATED APPLICATION DATA

This application claims the priority of U.S. Provisional Application No. 61/173,648, filed on Apr. 29, 2009, which is hereby incorporated in its entirety by reference.

FIELD OF THE INVENTION

The invention relates to a medical instrument comprising a signal transmitter and at least one activating device for activating the transmitter which is provided on a transmitter unit which is separate from the instrument.

BACKGROUND OF THE INVENTION

A generic instrument of this type is known from EP 1 990 021 A1, wherein in this case, a separate transmitter unit is provided which can be inserted into a sealable interior receptacle of an instrument. Such a solution requires special instruments to be provided and is therefore relatively costly.

Medical instruments such as are provided within the framework of the present invention can—in addition to their actual purpose as instruments—also be used to control treatment-assisting software. In computer-assisted surgery, the person performing the treatment is provided with different image outputs, in most cases by a navigation and/or tracking system in the operating theatre. These image outputs show patient data sets or at least parts of patient data sets, i.e. for example three-dimensional or sectional representations of parts of the patient's body. The patient data sets can be generated either by imaging methods such as for example CT or MR tomography, x-ray, ultrasound or fluoroscopy, or by imageless methods such as tapping a bone surface by means of a registered pointer tool, or using laser scanning. Within the framework of image assistance, it is also for example possible to show instruments or treatment devices in their positional relationship relative to the patient data, so as to visually assist the person performing the treatment. Depending on the progress of the treatment, it is often necessary to display a specific part of the software assistance on the screen output, namely the part comprising the functions which are currently required for the current step in the treatment. The software could also be said to consist of different "pages" which interchange in the course of the treatment. It is often necessary to select particular software pages during the treatment. In addition to the solution mentioned above, this is often also realized by means of an input apparatus such as a mouse or a keyboard or by means of a touch-sensitive screen. Foot switches, virtual keyboards or voice control systems are also known. Other "means of communication" are for example specific movements of tracked instruments, for example pivoting about a fixed point.

SUMMARY OF THE INVENTION

Against this background, it is the object of the present invention to optimize the transmission of signals for communication and control in conjunction with medical instruments. The intention is in particular to make equipping an instrument with signal-transmitting functionality simpler and/or applicable to conventional instruments.

This object is solved in accordance with the invention by a medical instrument comprising a signal transmitter and at least one activating device for activating the transmitter which is provided on a transmitter unit which is separate from the instrument, wherein the transmitter unit is a unit which can be fastened to the exterior of the instrument. The subclaims define preferred embodiments of the invention.

The invention is characterized in that the transmitter unit is a unit which can be fastened to the exterior of the instrument. In other words, a transmitter unit which can be placed on the instrument is provided, which makes equipping instruments with transmitter functionality significantly simpler. It is possible to provide transmitter units which can be fastened to conventional instruments easily and/or in simple steps, such that the need to provide special and therefore expensive instruments is removed. The invention is based inter alia on the recognition that the sterility of such instruments is not necessarily threatened if transmitter units are used which can be placed on the exterior of the instrument, and the reason for this is that such transmitter units can also be pre-sterilized in their entirety and in particular provided sterilely packaged. This enables a cost-effective solution without sterility problems; specifically, it is possible to circumvent the problems caused by hot-steam sterilization—which in practice is used the most—with electronic components and energy supply elements.

In one embodiment of the present invention, a positionally defined fixing portion for the transmitter unit is provided on the instrument, while on the other hand, the transmitter unit can also comprise a fastening portion which can be fastened to the periphery of the instrument, in particular to such a fixing portion.

In order to optimize handling, the transmitter unit can be able to be fastened by means of a releasable quick-release lock, in particular by means of a snap-on and/or plug connection. In accordance with one embodiment variant, it can be fastened using a fixing element which is arranged on the periphery of the instrument, in particular using a part of the instrument which can be detached and re-attached, specifically a reference marker which can be attached to the instrument.

The transmitter unit can include different functional elements, including: an optical transmitter, specifically an LED, in particular an infrared LED; and an activating switch, specifically a contact switch. In addition, an optical status signal emitter, in particular a status signal LED, can also be provided.

It is possible to embody the medical instrument such that the transmitter unit comprises an integrated energy supply for the transmitter, in particular a battery, specifically a button cell battery.

In a particularly preferred embodiment, the transmitter unit is provided as a disposable item, specifically as a sterilely pre-packaged disposable item which can for example be provided in situ in the operating theatre in a tear-open pack. Modern production methods allow such disposable items to be cost-effectively produced, for example substantially or mainly (predominantly) from a plastic material, and in operating theatres—in which sterility is an extremely important condition—such a practice is perfectly justified and is already used in various ways.

In accordance with another aspect, the present invention relates to a system of instruments comprising: a plurality of instruments such as are described here in different embodiments, wherein the instruments comprise standardized fixing portions which can fasten the same transmitter unit and/or a transmitter unit via identical standardized fastening portions;

and at least one separate transmitter unit. This embodiment variant enables the invention to be used universally with many different instruments.

Another aspect of the present invention relates to a method for controlling a treatment-assisting medical software by means of a signal transmitter which is arranged on a medical instrument. The medical instrument is positionally detected by means of a medical tracking system, and the software assigns a different significance to the signal output by the transmitter depending on the position of the instrument.

This system, in which instruments such as are described and claimed here can be used, enables a broad communications base and the transfer of different, even complicated control commands on the one hand, and on the other hand enables signal transmitter units to be held in a very simple way, since the invention envisages that the signal does not necessarily have to be changed in order to relay different commands, but rather it is merely necessary to simply change the position of the instrument on which the signal emitter is currently situated. Because such instruments, for example pointers, can be relatively simply moved to certain positions by the physician performing the treatment, the present invention enables a wealth of signals to be transferred by equipping an instrument in a simple way and/or using a simple transmitter.

In a specific embodiment of the method in accordance with the invention, at least one spatial region is defined within the detection range of the tracking system, in particular in the vicinity and/or environment of a tracking reference, wherein the signal output by the transmitter is given a particular significance by the software when the instrument interacts with this spatial region, in particular when the tip (or a particular part) of the instrument is situated in this spatial region.

It is also possible to transmit an instrument identification signal or code by means of the signal transmitter, which can make initializing (and/or calibrating) the instruments, for example for an operation-accompanying medical navigation system, much simpler.

In accordance with other aspects, the invention relates to a program which, when it is running on a computer or is loaded on a computer, causes the computer to perform a method such as is described here, and to a computer program storage medium comprising such a program.

BRIEF DESCRIPTION OF THE DRAWINGS

The invention is explained below in more detail on the basis of an embodiment. It can comprise any of the features described here, individually and in any combination, and can in particular also be regarded as the use of a separate signal transmitter, which can be placed on the exterior of the instrument, for software control.

DETAILED DESCRIPTION

In the enclosed drawings, an embodiment of a transmitter unit in accordance with the invention is indicated by the reference sign 1. It comprises a body including a fastening portion 2 and an extension and/or LED support 3 which comprises a signal LED 5 and a status LED 4. Opposite the support 3, the activating switch 6—in this case, a contact switch—is attached to the fastening portion 2. The switch 6 can be any switch, including for example a push-button switch.

Figure 1:
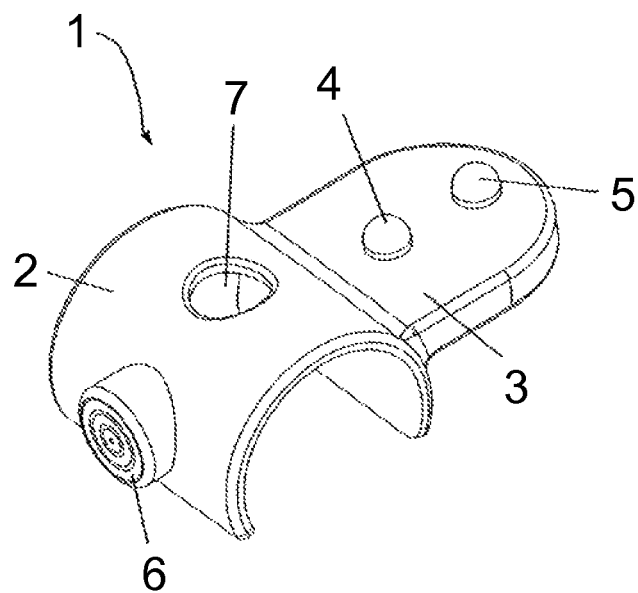
FIGS. 1 to 3 show an embodiment of a transmitter unit in accordance with the invention.
Figures 2, 3:
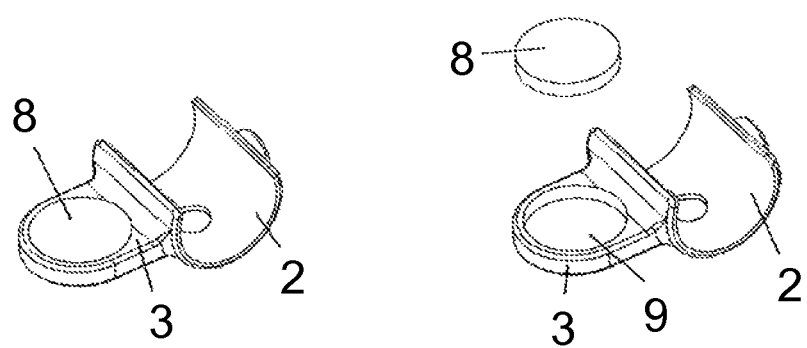

A cavity 9 is provided in the lower part of the support 3 for a button cell battery 8 which provides the energy supply for emitting signals through the LEDs 4, 5. A passage 7—in this case, a circular hole—is situated in the upper part of the fastening portion 2. The aforesaid component designations can in particular be gathered from FIGS. 1 to 3.

Figure 4:
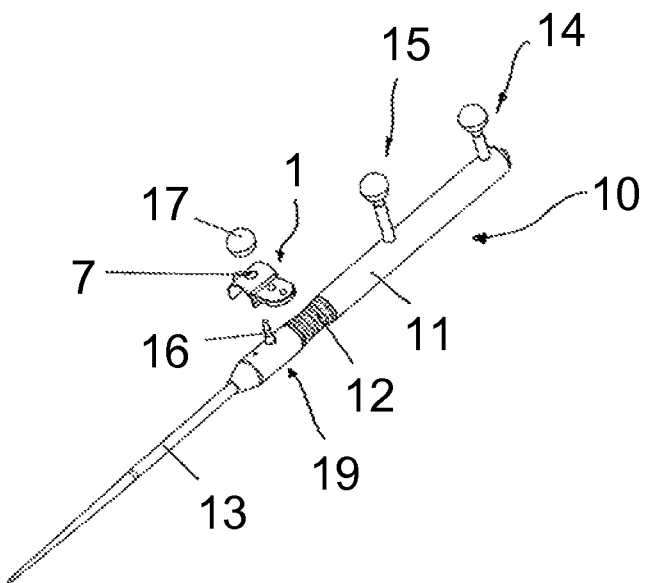
FIGS. 4 and 5 show a medical instrument equipped with a transmitter unit.
Figure 5:
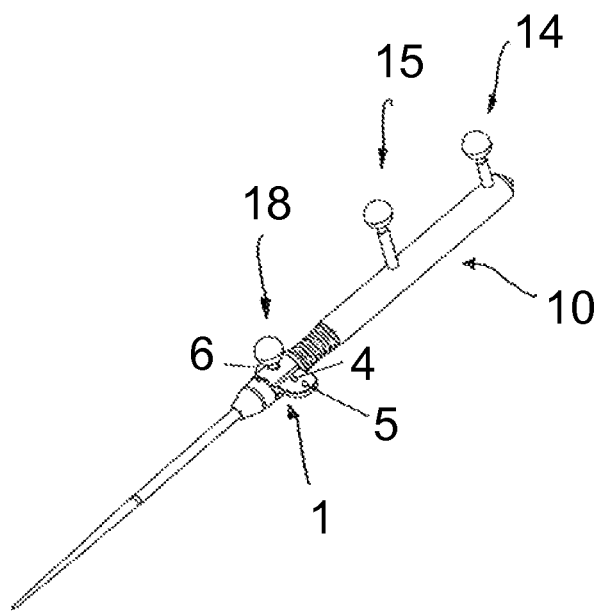
Figure 7:
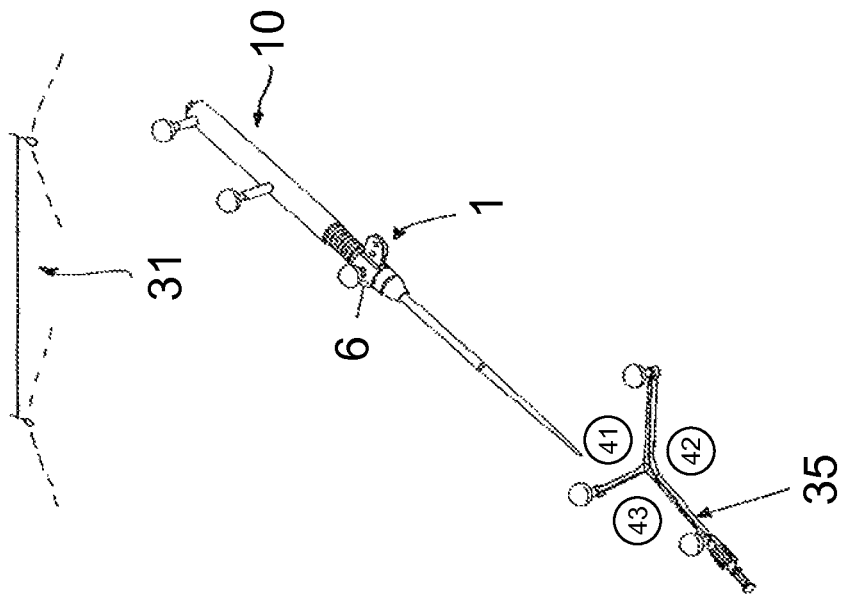
FIGS. 6 and 7 show two embodiments for transferring signals in accordance with the position of the instrument.
Figure 6:
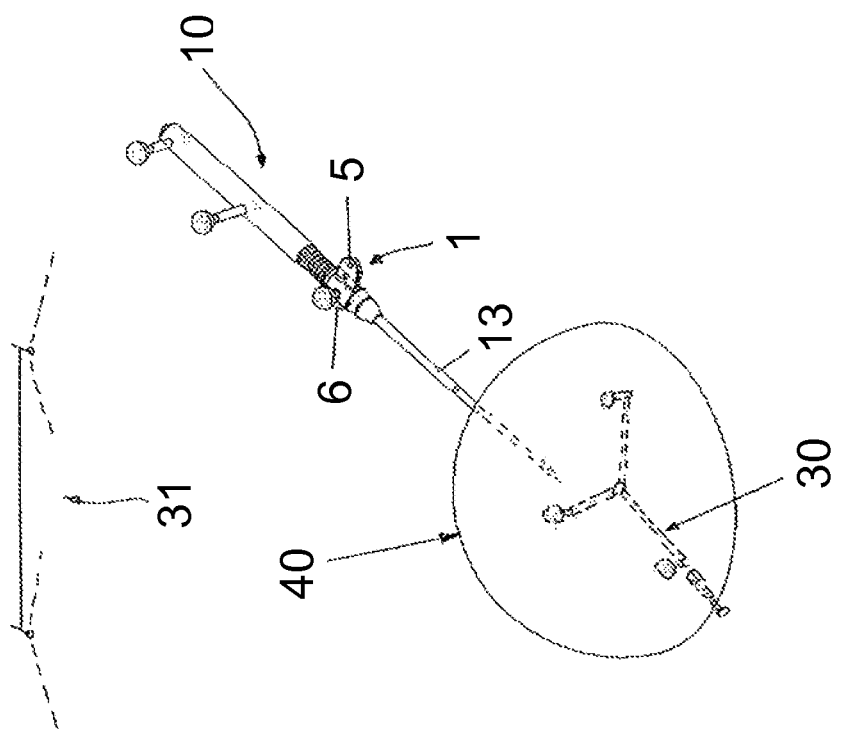

FIGS. 4 to 7 show an instrument 10 which comprises an instrument grip 11 and a tip 13 and which is embodied as a pointer and/or pointing apparatus. The grip has a corrugated portion 12 at which it can be securely held, and three reference markers 14, and 18 protrude upwards out of the grip and serve as tracking markers for a medical tracking system 31 which comprises two tracking cameras which are schematically shown in FIGS. 6 and 7 but not separately indicated. The foremost tracking marker 18 is shown in more detail in FIG. 4 and comprises the protruding marker holder 16 and the marker sphere 17 on the fixing portion 19. As can be gathered from FIGS. 4 and 5, the transmitter unit 1 in this embodiment is plugged onto the marker holder 16 using the transit hole 7 and then onto the fixing portion 19 and is fixed and/or secured against being unintentionally lost by screwing-on the marker sphere 17.

FIGS. 6 and 7 also show different defined spatial regions 40, 41, 42 and 43 which are formed and/or defined around tracking references 30 and/or 35. The subsequent description of the invention will now be based on said figures and designations.

Like any standard navigation instrument comprising passive tracking technology, the instrument 10 also has reflection markers 14, 15 and 18, and these markers and/or their reflective spheres (for example, 17) reflect emitted infrared light and are thus positionally detected by the tracking system 31. Conventional navigation systems use these position data as three-dimensional position information for particular marker geometries and assign it to particular instruments, such that the navigation system always for example knows where the front end of the tip 13 of the instrument 10 is situated.

The transmitter unit 1 in accordance with the present invention, which can be regarded as an active input device for software control, is fastened to an instrument marker 18 on the instrument 10 as shown in FIGS. 4 and 5 and as already described above. In this position, the switch 6 can easily be reached by a finger; when it is activated, the infrared LED 5 emits an infrared light signal for software control, which is for example detected by the tracking system 31, and the LED 4 emits a visible light signal as a confirmation or status signal, so that the user knows that the invisible infrared signal of the LED 5 has indeed also been transmitted. As already indicated above, the power supply for this is provided by the button cell 8 in the battery holder 9.

The transmitter unit 1, which in this case is produced from plastic as a disposable item, is advantageously designed such that it can be attached symmetrically, such that it can be attached to the instrument universally for right-handed or left-handed operation, i.e. with the support extension 3 aligned in one or other direction of the instrument body, away from its longitudinal axis. In the preferred embodiment, the transmitter unit 1 is attached at a defined position on the navigated instrument 10, namely to the fixing portion 19, such that the software can identify the positional range of the infrared LED support signal, which is stored in the navigation system together with the geometric information about the instrument 10.

When the activating switch 6 is activated, the infrared LED signal of the diode 5 is activated. During this "active mode", the LED 5 is tracked by the tracking cameras of the tracking system 31, and the signal emitted is used to control a software functionality of the navigation system, for example as a confirmation signal.

The positional accuracy of the infrared LED 5 is then less important, because only the more exactly positioned passive markers 14, 15 and 18 reference the instrument geometry. For this reason, the transmitter unit can be designed very simply and cheaply, as a sterile disposable item. In another embodiment, active trigger signals could be used to digitize registration points on objects, for example bone surfaces, without having to generate additional trigger movements or other trigger signals.

With respect to applicability, active disposable transmitter units in accordance with the invention can be universally used in combination with any possible existing passive instruments and pointing apparatuses (pointers), and already-existing passive pointer apparatuses can therefore be equipped and/or augmented with active control functionalities. The transmitter units could also be embodied to be compatible with other passive navigated instruments, for example drill guides, cutting blocks, awls, broaching tools, etc., wherein they would likewise be fastened (as disposable items) to these instruments and detached again after use. If such sets of instruments are provided, they could have specifically assigned and embodied interfaces for attaching the universal disposable transmitter units. Other technical features can be integrated, such as additional infrared LEDs, wireless RF communications modules or a plurality of control buttons, which would increase functionality even further, in particular also with regard to the software interaction for standard passive instruments.

Another aspect of the invention, which may be referred to as non-contact software workflow control, shall now be explained in more detail by referring specifically to FIGS. 6 and 7. During medical navigation, reference arrays 30, 35 are usually provided and fastened to the patient, in order to be able to reproduce the patient's movements and integrate them into navigation. On the basis of these reference geometries 30, 35 (or also on the basis of other reference geometries provided), it is then possible to determine pre-defined virtual spatial regions which can serve as a remote control for using the instrument. If, for example, a pointed end of a navigated instrument is introduced into such a remote control region, for example the region 40 around the reference array 30 in FIG. 6, a particular "remote control mode" for the software is launched.

In the case of "one-button" control, the user can then control functionalities of the active transmitter unit in order to communicate simple commands such as "next", "back" or "select". Thus, "next" functions can for example be assigned to short signals (less than 0.5 seconds), while activating the switch 6 for longer (more than one second) can be classified and pre-defined as a "back" command, when the tip 13 of the pointer instrument 10 is situated in the virtual region 40 around the reference array 30. If a different function, for example a "select" function, is then required, the user can remove the front end of the tip 13 from the virtual region 40 around the reference array 30, and when the tracking and navigation system determines that this tip end is not situated in the region 40, a different command is assigned to activating the switch 6, for example a "select" command. Subsequent clicks on the active input device 1 would then for example confirm, select, activate or digitize reference points on parts of the patient's body. Using a "sustained" activation of the button and/or signal emitter, it is also possible to register multiple surfaces, wherein the tip of the pointer instrument is guided over the surface to be registered, and the software ensures that points are not repeatedly recorded.

The remote control regions 40 in accordance with the invention are situated in a freely defined and definable space around the reference array 30.

Another embodiment, shown in FIG. 7, provides for subdividing the remote control region into three free regions 41, 42 and 43 between the arms of the reference star 35. Each region then has a different functionality when the pointer tip is introduced into it, and corresponding functionalities can be accessed by pressing the activating switch 6, wherein the tip of the pointer can remain spatially free and does not have to contact the reference star 35 at predetermined or pre-defined locations, such that shifts in references and resultant registration inaccuracies are avoided.

The embodiments of the present invention thus enable a non-contact, wireless and very comfortable interaction between the person performing the treatment and a software of a navigation system. The person performing the treatment controls the functionalities of the system by using a navigated instrument in the sterile environment. By assigning an active interaction device to the passive navigated instrument, the range of possible methods is extended and allows a greater variety of control inputs (for example, during registration), without having to perform the movements or perform separate selecting or confirming controls. The transmitter unit can be placed, as a disposable item and active auxiliary element, onto existing passive navigated instruments (for example as a clip), and it is thus possible to avoid problems which arise, due to integrated electronics, when heat and steam are used in sterilizations.

The advantages of the invention in general and of different specific embodiments of the invention can also be listed as follows:

an intuitive interaction between the user and the software/computer system is possible;

objects can be registered in the navigation system more comfortably, easily and quickly;

slipping during object registration, for example bone registration, can be avoided because confirming movements are avoided (pivoting);

it becomes possible to optimally align reference arrays for the best possible recognition/accuracy during registration (pivoting movements through regions with restricted visibility is not required);

user flexibility is provided;

a simple instrument design is possible;

there is no need for autoclaving, such that damage to electronic components and energy supply elements can be avoided;

there is compatibility with existing passive instruments, such as for example pointers; and any passive instrument can be upgraded with additional active functionalities.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. An apparatus comprising:
   a medical instrument having a marker mount for receiving a detachable reference marker, wherein the medical instrument includes a positionally defined fixing portion; and
   a signaling device for the medical instrument, the signaling device comprising:
      a transmitter unit including a transmitter unit mount, the transmitter unit mount different from the marker mount, the transmitter unit further comprising a fastening portion which is detachably couplable to the periphery of the instrument;
      a signal transmitter; and
      at least one activating device for activating the transmitter, wherein the transmitter unit mount is fixed and/or secured to the instrument by the detachable reference marker;
   wherein the fastening portion is configured to cooperate with the fixing portion to couple the transmitter unit to the medical instrument.

2. The medical instrument according to claim 1, further comprising a quick-release lock configured to removably couple the transmitter unit to the medical instrument, wherein the quick-release lock is arranged on the periphery of the instrument.

3. The medical instrument according to claim 1, further comprising the detachable reference marker.

4. The medical instrument according to claim 1, wherein the transmitter unit comprises an optical transmitter and an activating switch.

5. The medical instrument according to claim 4, wherein the optical transmitter is an LED.

6. The medical instrument according to claim 5, wherein the LED is an infrared LED.

7. The medical instrument according to claim 4, wherein the activating switch is a contact switch.

8. The medical instrument according to claim 1, wherein the transmitter unit comprises an optical status signal emitter.

9. The medical instrument according to claim 8, wherein the optical status signal emitter is a status signal LED.

10. The medical instrument according to claim 1, wherein the transmitter unit comprises an integrated energy supply for the transmitter.

11. The medical instrument according to claim 10, wherein the integrated energy supply for the transmitter is a battery.

12. The medical instrument according to claim 11, wherein the battery is a button cell battery.

13. The medical instrument according to claim 1, wherein the transmitter unit is a disposable item.

14. A system of instruments, comprising:
   a plurality of instruments in accordance with claim 1, which comprise standardized fixing portions which can fasten the same transmitter unit and/or transmitter units via identical standardized fastening portions; and
   at least one separate transmitter unit.

* * * * *